US00PP36223P2

(12) United States Plant Patent
Danziger

(10) Patent No.: US PP36,223 P2
(45) Date of Patent: Oct. 22, 2024

(54) ***CALIBRACHOA* PLANT NAMED 'DCALCOTNG'**

(50) Latin Name: ***Calibrachoa* hybrid**
Varietal Denomination: DCALCOTNG

(71) Applicant: Danziger 'DAN' Flower Farm, Beit Dagan (IL)

(72) Inventor: Gavriel Danziger, Beit Dagan (IL)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 18/389,380

(22) Filed: Nov. 14, 2023

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413

CPC . A01H 5/02; A01H 5/00; A01H 6/821; A01H 6/82
See application file for complete search history.

(56) References Cited

PUBLICATIONS

BFG Supply Co. Spring Trials 2023 Report, retrieved on Mar. 11, 2024 at https://www.bfgsupply.com/media/7520/2023-pc-spring-trials_web.pdf, 2 cover pages, p. 1 and 2 back cover pages. (Year: 2023).*

* cited by examiner

*Primary Examiner* — June Hwu
(74) *Attorney, Agent, or Firm* — Cassandra Bright

(57) ABSTRACT

A new and distinct *Calibrachoa* cultivar named 'DCALCOTNG' is disclosed, characterized by a semi-trailing plant habit. Plants produce an abundance of light orange colored flowers with yellow throats. Plants begin flowering early, and are day length neutral. The new variety is a *Calibrachoa*, normally produced as an outdoor garden or container plant.

2 Drawing Sheets

Figure 1:
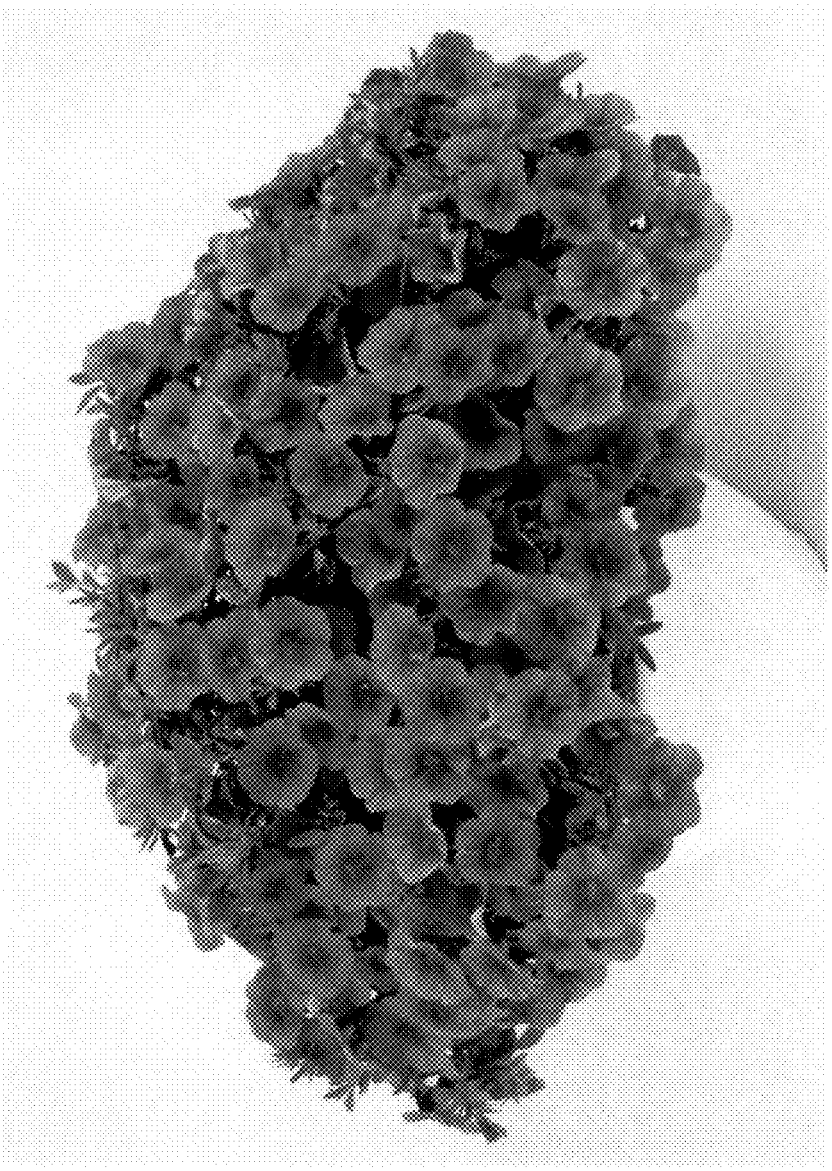

Latin name of the genus and species: *Calibrachoa* hybrid. Variety denomination: 'DCALCOTNG'.

BACKGROUND OF THE INVENTION

The new *Calibrachoa* cultivar is a product of a planned breeding program conducted by the inventor, Gavriel Danziger in Moshav Mishmar Hashiva, Israel. The objective of the breeding program was to produce new *Calibrachoa* varieties. The cross resulting in this new variety was made during November of 2019.

The seed parent is the unpatented, propriety variety referred to as *Calibrachoa* 'CA-18-7006'. The pollen parent is the unpatented, propriety variety referred to as *Calibrachoa* 'CA-18-6904'. The new variety was discovered in May of 2020 by the inventor in a group of seedlings resulting from the parental crossing, in a greenhouse in Moshav Mishmar Hashiva, Israel.

Asexual reproduction of the new cultivar 'DCALCOTNG' was first performed by terminal vegetative cuttings during May of 2020, at a greenhouse in Moshav Mishmar Hashiva, Israel. Subsequent propagation by has shown that the unique features of this cultivar are stable and reproduced true to type in successive generations. First public access to plants of the variety occurred Dec. 18, 2022 in the Israel. This offer came directly or indirectly from the inventor, qualifying for the exception allowed under 102(b). Previous to this sale, although the variety may have been publicized in print, plants were not available to the public for propagation.

SUMMARY OF THE INVENTION

The cultivar 'DCALCOTNG' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCALCOTNG' These characteristics in combination distinguish 'DCALCOTNG' as a new and distinct *Calibrachoa* cultivar:

1. Light orange flower color.
2. Early flowering.
3. Day-length neutral.
4. Semi-trailing plant habit.

PARENT COMPARISONS

Plants of the new cultivar 'DCALCOTNG' are similar to plants of the seed parent in most horticultural characteristics, however, plants of the new cultivar 'DCALCOTNG' differ in the following;

1. The new variety has a semi-trailing growth habit, while the seed parent has a trailing habit.
2. Flower color of the new variety is light orange, while the flower color of the seed parent is light red.
3. The new variety flowers earlier than the seed parent.

Plants of the new cultivar 'DCALCOTNG' are similar to plants of the pollen parent in most horticultural characteristics however, plants of the new cultivar 'DCALCOTNG' differ in the following;

1. The new variety has a semi-trailing growth habit, while the pollen parent has a mounded habit.
2. Flower color of the new variety is light orange, while the flower color of the pollen parent is faded red.

COMMERCIAL COMPARISON

Plants of the new cultivar 'DCALCOTNG' can be compared to the patented commercial variety *Calibrachoa* 'DACALCORANG' U.S. Plant Pat. No. 30,165. These varieties are similar in most horticultural characteristics; however, 'DCALCOTNG' differs in the following:

1. Flower color of the new variety is light orange, while the flower color of this comparator is dark orange.
2. The new variety flowers earlier than this comparator.
3. Plants of the new variety are not as heat resistant as plants of this comparator.

BRIEF DESCRIPTION OF THE PHOTOGRAPHS

The accompanying photograph in FIG. 1 illustrates in full color a typical plant in a 20 cm pot, at approximately 5 months of age, of 'DCALCOTNG' grown in a greenhouse, in Moshav Mishmar Hashiva, Israel.

Figure 2:
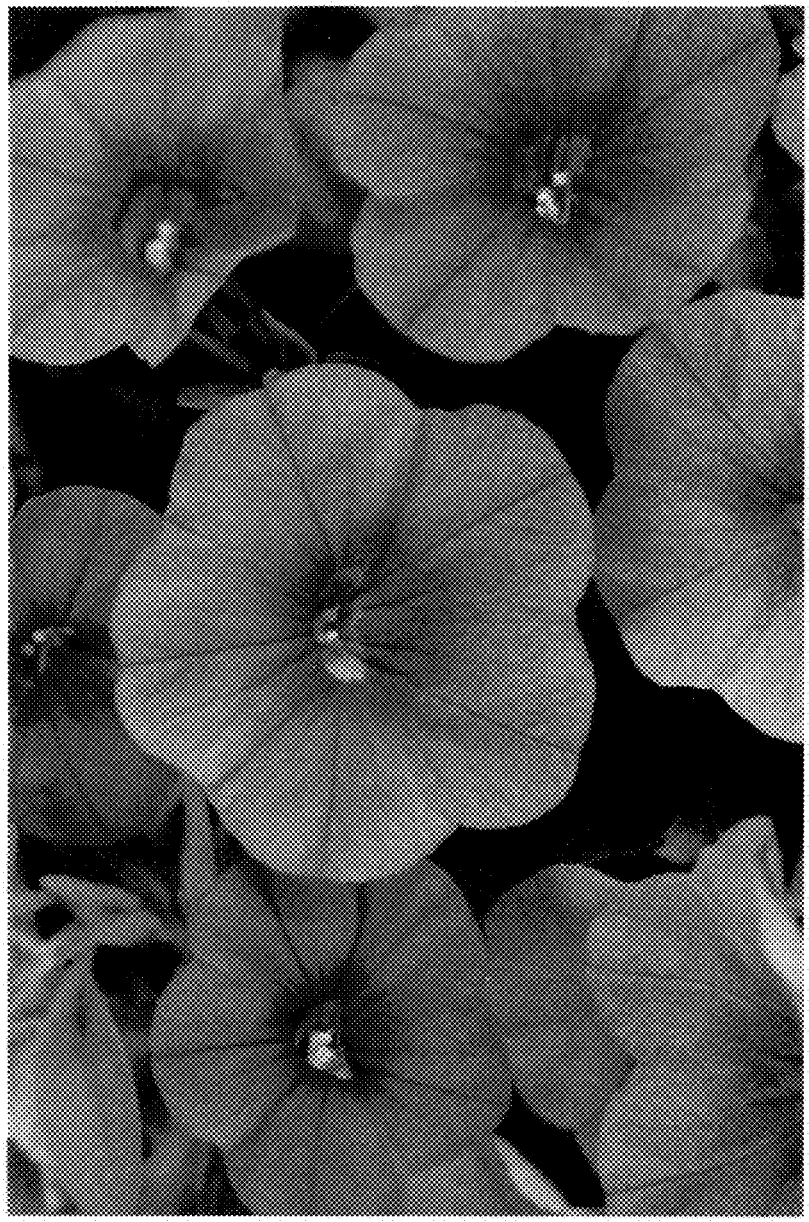

FIG. 2 illustrates in full color typical flowering plants of 'DCALCOTNG' grown in 12 cm pots in early Spring, during days having 10 hours of light.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCALCOTNG' plants grown in greenhouse in Moshav Mishmar Hashiva, Israel, under natural lighting. Measurements were taken during spring of 2023. The plants were approximately 50 days from a rooted cutting in a 12 cm pot. The growing temperature ranged from 15° C. to 28° C. during the days, 15° C. to 20° C. during the nights. Measurements and numerical values represent averages of typical plant types.

Botanical classification: *Calibrachoa* 'DCALCOTNG'.

PROPAGATION

Time to initiate roots: 10 to 15 days at approximately 18° C.
Root description: Fibrous.

PLANT

Growth habit: Semi-trailing.
Pot size of plant described: 12 cm.
Height: About 13 cm to top of flowering plane.
Plant spread: 32 cm.
Growth rate: Medium.
Length of primary lateral branches: 20 cm.
Diameter of lateral branches: 0.3 cm.
Quantity of primary lateral branches: 4.
Characteristics of primary lateral branches:
- *Form.*—Cylindrical.
- *Diameter.*—0.3 cm.
- *Color.*—RHS Yellow-Green 146C.
- *Texture.*—Scabrous.
- *Strength.*—Good.

Internode length: 1 to 1.5 cm.

FOLIAGE

Leaf:
- *Arrangement.*—Alternate.
- *Quantity.*—Approximately 40 per branch.
- *Average length.*—2.8 cm.
- *Average width.*—1.1 cm.
- *Shape of blade.*—Elliptic.
- *Apex.*—Rounded.
- *Base.*—Acuminate.
- *Margin.*—Entire.
- *Texture of top surface.*—Glabrous.
- *Texture of bottom surface.*—Scabrous.
- *Pubescence.*—Scabrous.
- *Aspect.*—90°.
- *Color.*—Young foliage upper side: RHS Green 137B. Young foliage under side: RHS Yellow-Green 147B. Mature foliage upper side: RHS Green 137B. Mature foliage under side: RHS Yellow-Green 147B.
- *Venation.*—Type: Pinnate. Venation color upper side: RHS Green 137A. Venation color under side: RHS Yellow-Green 147B.
- *Petiole.*—Length: 1 to 2 mm. Diameter: 1 mm. Color: RHS Green 137B. Texture: Glabrous.

FLOWER

Natural flowering season: All year in Beit Dagan, Israel.
Days to flowering from rooted cutting: 20 to 30 days.
Inflorescence and flower type and habit: Panicle.
Rate of flower opening: 2 to 3 days from bud to fully opened flower.
Flower longevity on plant: 4 to 7 days.
Flower lobing intensity: Weak to medium.
Flowers per panicle: Average range 3 to 7.
Approximate quantity of flowers per plant: About 70.
Persistent or self-cleaning: Self-cleaning.

Bud:
- *Shape.*—Ovoid.
- *Length.*—0.2 to 0.3 cm.
- *Diameter.*—0.15 cm.
- *Color.*—RHS Yellow-Green 145C.

Flower size:
- *Diameter.*—3.5 to 4 cm.
- *Length.*—3.5 to 4 cm.
- *Flower tube diameter at distal end.*—0.3 cm.
- *Flower tube diameter at proximal end.*—1.1 cm.

Petals:
- *Length from throat.*—1.5 to 2 cm.
- *Width.*—1.8 to 2 cm.
- *Quantity.*—5.
- *Texture.*—Glabrous.
- *Apex.*—Rounded.
- *Margin.*—Entire.

Color:
- *When opening.*—Upper surface: RHS Red-Orange 34A flushed Red 46A at transition to corolla tube. Veins near Red 46A. Lower surface: RHS Yellow-Pink 38B.
- *Fully opened.*—Upper surface: RHS Red-Orange 40A flushed Red 45C at transition to corolla tube. Veins strongly conspicuous, colored near Red 46A. Lower surface: RHS Yellow-Pink 38B. Flower throat (inside): RHS Yellow 7A. Flower throat, vein: RHS Red 46A. Flower tube (outside): RHS Yellow 1D. Flower tube, vein: RHS Red 46C. Petal color, fading to: RHS Red-Orange 40D.

Calyx/sepals:

*Quantity per flower.*—5.
*Shape*.—Lanceolate.
*Length.*—1.5 cm.
*Width.*—0.4 cm.
*Apex*.—Rounded.
*Base*.—Cuneate.
*Margin*.—Entire.
*Texture*.—Glabrous.
*Color*.—Upper Surface: RHS Yellow-Green 147B. Lower Surface: RHS Yellow-Green 147C.

Peduncle: None present, pedicels emerging from branch.

Pedicel:

*Length.*—3 cm.
*Diameter.*—0.01 cm.
*Color*.—RHS Yellow-Green 144A
*Orientation.*—45 degrees
*Texture*.—Glabrous.
*Strength.*—Moderate.

Fragrance: None.

REPRODUCTIVE ORGANS

Stamens:

*Number.*—5.
*Filament length.*—0.8 to 1.3 cm.

Anthers:

*Length.*—0.15 cm.
*Shape*.—Globose.
*Color*.—RHS Yellow 9C.
*Pollen*.—Color: RHS Yellow 6C. Quantity: Small amount.

Pistil:

*Number.*—1.
*Length,*—1.2 cm.
*Style*.—Length: 0.9 cm. Color: RHS Green 138B.
*Stigma*.—Shape: Oblate. Color: RHS Green 138A. Ovary Color: RHS Yellow-Green 145B.

OTHER CHARACTERISTICS

Seeds and fruits: About 30 dark brown, rounded seeds of about 0.5 mm in diameter, per one brown, conical capsule.

Disease/pest resistance: Typical to known *Calibrachoa* varieties. Neither resistance nor susceptibility to the normal diseases and pests of *Calibrachoa* have been observed. Pests common to *Calibrachoa* include aphids and thrips. Typical diseases are *Botrytis* and *Pythium.*

Temperature tolerance: 5° C. to 30° C.

Drought tolerance: No tolerance for drought.

What is claimed is:

1. A new and distinct cultivar of *Calibrachoa* plant named 'DCALCOTNG' as herein illustrated and described.

* * * * *